United States Patent [19]

Patillo et al.

[11] Patent Number: 5,073,696
[45] Date of Patent: Dec. 17, 1991

[54] ELECTRICALLY HEATED WAX SHAPING TOOL

[75] Inventors: Ronald L. Patillo, Houston, Tex.; Charles E. Steele, Battle Creek, Mich.

[73] Assignee: Kerr Manufacturing Company, Romulus, Mich.

[21] Appl. No.: 412,679

[22] Filed: Sep. 26, 1989

[51] Int. Cl.⁵ .................. H05B 1/00; H05B 3/00; B23K 3/00
[52] U.S. Cl. .................. 219/233; 30/140; 219/229; 219/533; 228/51; 401/1
[58] Field of Search .............. 219/233, 235, 240, 221, 219/227, 229, 533; 30/140; 228/51-55; 401/1, 2

[56] References Cited

U.S. PATENT DOCUMENTS

| 410,330 | 9/1889 | Porterfield et al. . |
| 485,358 | 11/1892 | Soderin . |
| 923,717 | 6/1909 | Shepard . |
| 1,151,352 | 8/1915 | Frink .................. 219/233 X |
| 1,754,330 | 7/1928 | Litomy . |
| 1,769,437 | 7/1930 | Kromer, Jr. . |
| 2,101,913 | 12/1937 | Meyer .................. 219/233 X |
| 2,235,519 | 3/1940 | Hausknecht . |
| 2,272,780 | 2/1942 | Schweyer . |
| 2,405,866 | 8/1946 | Weller . |
| 2,501,192 | 3/1950 | Scholler .................. 219/233 |
| 2,734,986 | 2/1956 | Gameros .................. 219/235 X |
| 2,826,667 | 3/1958 | Brillinger . |
| 2,935,593 | 5/1950 | Fulmer . |
| 2,960,591 | 11/1960 | Brillinger . |
| 2,973,422 | 2/1961 | Smith . |
| 3,169,499 | 2/1965 | Armanno . |
| 3,211,354 | 10/1965 | Dugard et al. . |
| 3,392,897 | 7/1968 | Siegel . |
| 3,422,247 | 1/1969 | Royston et al. . |
| 3,526,750 | 9/1970 | Siegel .................. 219/233 |
| 3,558,854 | 1/1971 | Siegel et al. . |
| 3,578,948 | 5/1971 | Fround et al. . |
| 3,702,916 | 11/1972 | Christensen . |
| 3,711,211 | 1/1973 | Garrison . |
| 3,742,187 | 6/1973 | Folus .................. 219/233 X |
| 3,821,513 | 6/1974 | Christensen .................. 219/233 |
| 4,367,396 | 1/1983 | Ravinsky .................. 219/233 |
| 4,495,403 | 11/1985 | Attila .................. 219/233 |
| 4,798,934 | 1/1989 | Boyer .................. 219/233 |
| 4,822,979 | 4/1989 | de Kam .................. 219/233 X |

FOREIGN PATENT DOCUMENTS

| 897721 | 6/1944 | France . |
| 424218 | 8/1947 | Italy .................. 219/235 |
| 1004034 | 3/1983 | U.S.S.R. .................. 219/233 |

Primary Examiner—Anthony Bartis
Attorney, Agent, or Firm—Marjama & Pincelli

[57] ABSTRACT

A tool for shaping wax and wax-like substances has a handpiece containing an electrical connector for connection to a source of electrical power and an opening in which an electrically heated tool tip is removably mounted for the convenient interchange of tips. The tool tip is held in a fixed predetermined position in the opening by ridges in the opening interlocked with complementary notches on the tip and is removably mounted within the opening in electrical connection with the connector. A cooling air gap is formed between the outer surface of said tip and the inner surface of said opening by the interlocked ridges and notches to prevent overheating of the handpiece. The tip comprises two spaced apart electrically conductive parallel wires which are connected at one end to form a continuous tip which defines a confined air gap of a defined configuration which is suitable for holding and shaping wax.

6 Claims, 5 Drawing Sheets

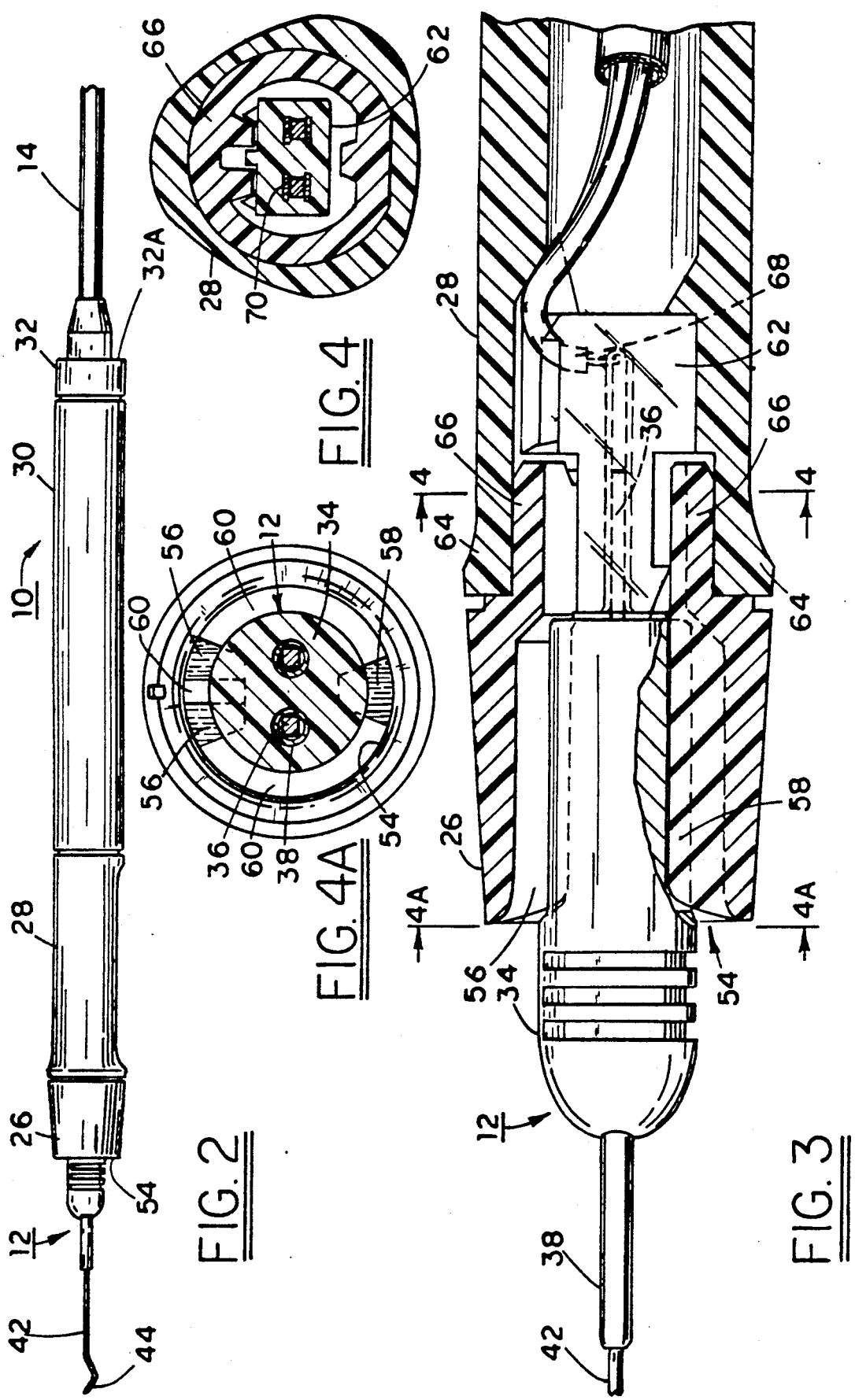

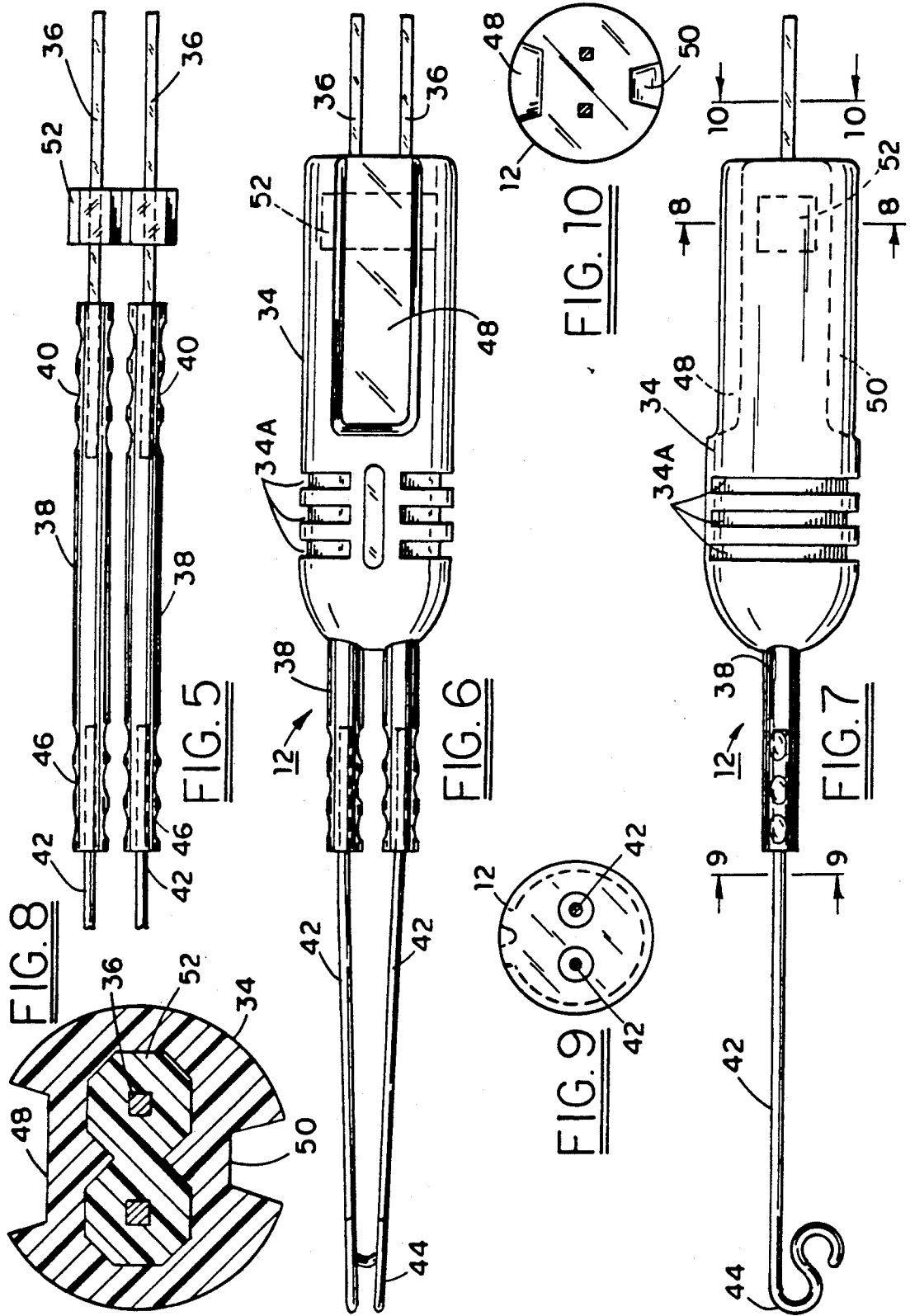

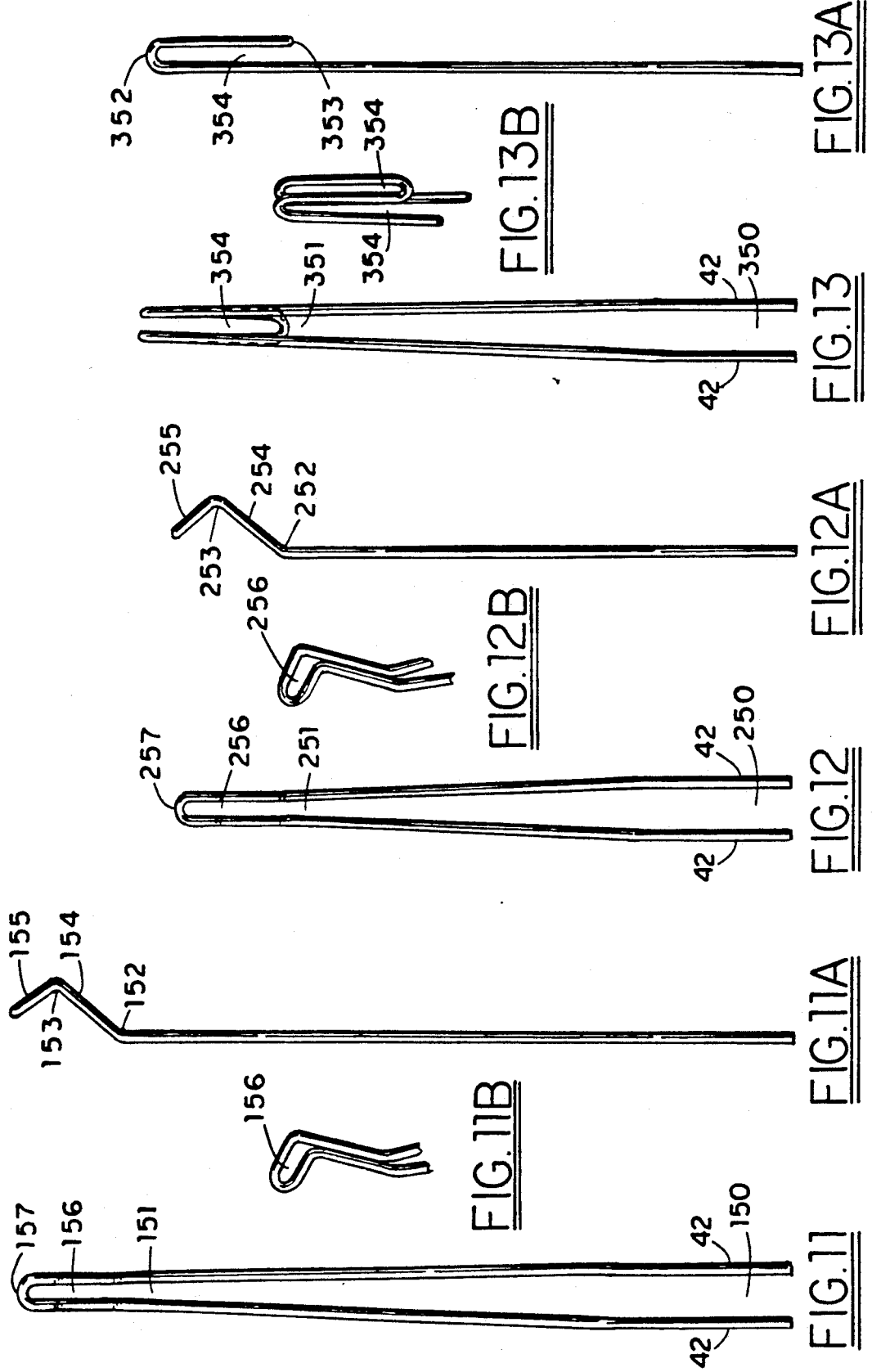

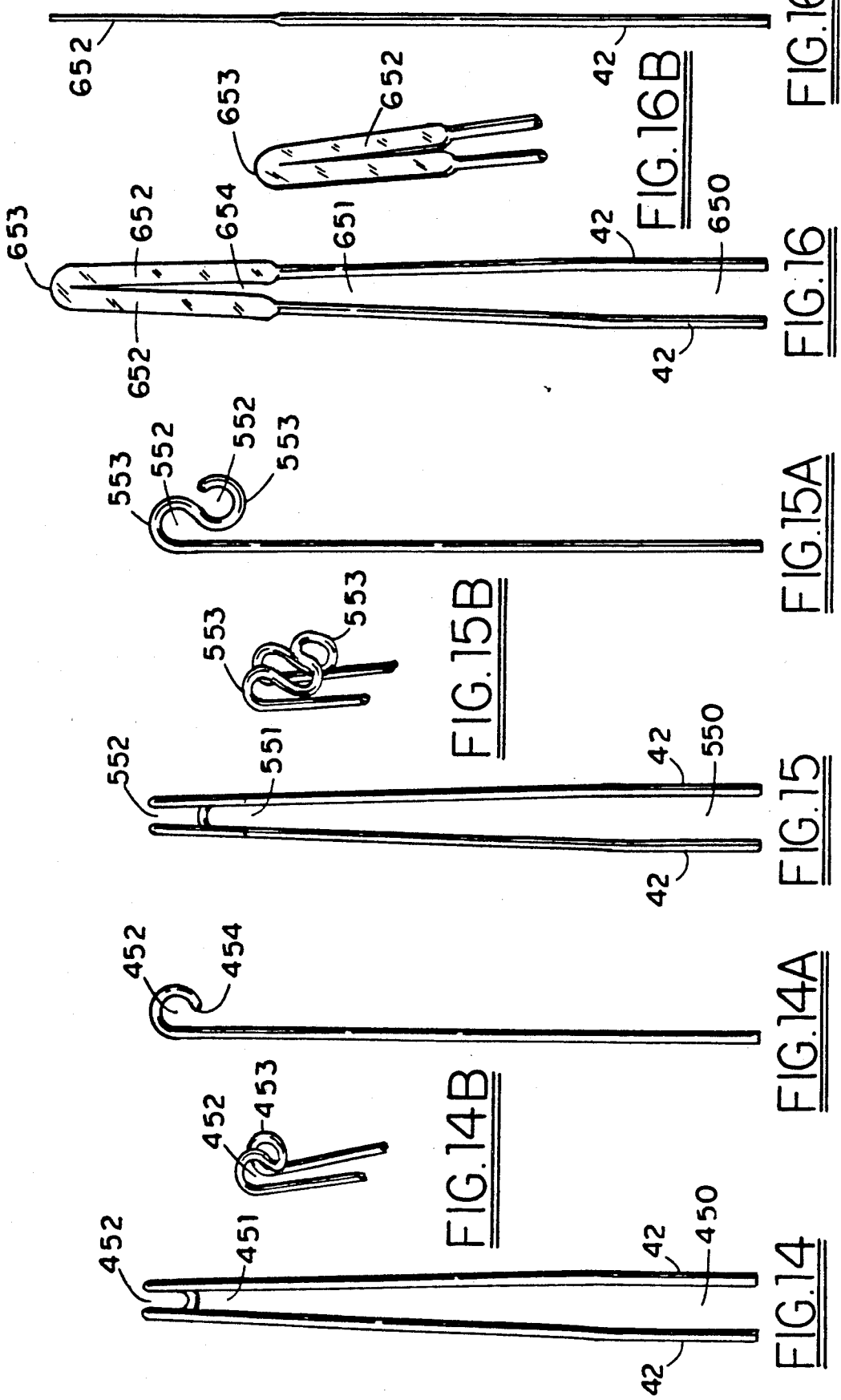

ELECTRICALLY HEATED WAX SHAPING TOOL

BACKGROUND OF THE INVENTION

The present invention relates to a wax shaping tool and more specifically, to a tool which may be used to shape and design wax models for use in making jewelry. The tool also finds utility and other fields in which wax patterns are formed such as dentistry and art.

SUMMARY OF THE INVENTION

The present invention is related to a wax shaping tool utilizing a removable electrically conductive heat conducting tip portion of fine gauge metallic wires which allows highly intricate work to be carried out in forming and shaping wax models. The wax shaping tool of the present invention includes a handpiece which comprises a handle which at one end includes an open cylindrical end to accommodate the removable wax shaping tip. The opposite end of the handpiece has an open end which accommodates a connection for an electrical cord. The handpiece may be made of any suitable high temperature plastic. When the removable tip is in place in the handpiece, the electrical plug section of the tip and the larger internal diameter of the opening of the handpiece combine to form circumferentially extending air gaps which provides a unique configuration for assisting in keeping the handpiece cool, such that finger gripping at the end is comfortable to the user. The tip ends used in the present invention have a much finer wire gauge than is presently available in the prior art, and therefore are able to be used to attain more precise and finer work than presently available in the art. Furthermore, the fine wire gauge in conjunction with the novel tip configuration at the end of the wire allow the tips to hold a greater amount of wax than tools of the prior art. The tips also provide a convenient ease of changing from one tip configuration to another in order to provide greater versatility and convenience in carrying out various functions in forming wax molds or patterns. Basically, the tip configuration used with the present tool comprise two spaced apart substantially parallel conductive wires which are connected at a tip end in a novel configuration which, through the use of capillary action and other advantages set forth herein, provide great versatility and touch in forming intricate wax patterns. Basically these tip configurations are either in the form of a bent end tip, rounded end tip, or spatula tip, which provide the user a great versatility with regard to carrying out various functions in working on wax models.

BRIEF DESCRIPTION OF THE DRAWINGS

FIG. 2 illustrates a side view of the handpiece with one embodiment of a wax shaping tip;

FIG. 3 illustrates a side sectional view of one end of the handpiece with the electrical connection and the socket connection for a wax shaping tip;

FIG. 4 is a sectional view through line 4 of FIG. 3 illustrating the socket connection of the handpiece.

FIG. 4A is a sectional view through line 4A—4A of FIG. 4;

FIG. 5 illustrates the connecting means for the wires of the tip;

FIG. 6 is a side sectional view illustrating the complete tip and socket section which is plugged into the handpiece;

FIG. 7 is a side sectional view of FIG. 6;

FIG. 8 is a sectional view through line 8—8 of FIG. 7;

FIG. 9 is a sectional view through line 9—9 of FIG. 7;

FIG. 10 is a sectional view through line 10—10 of FIG. 7;

FIGS. 11, 11A and 11B are front, side and perspective views of one embodiment of a long bent shaping tip of the present invention;

FIGS. 12, 12A and 12B are front, side and perspective views of a short bent shaping tip of the present invention;

FIGS. 13, 13A and 13B are front, side and perspective views of a folded straight tip of the present invention;

FIGS. 14, 14A and 14B are front, side and perspective views of a round nose shaping tip of the present invention;

FIGS. 15, 15A and 15B are front, side and perspective views of a squiggle or S configuration shaping tip of the present invention; and FIGS. 16, 16A and 16B are front, side and perspective views of a rolled flat spatula shaping tip of the present invention.

DETAILED DESCRIPTION OF THE INVENTION

Figure 1:
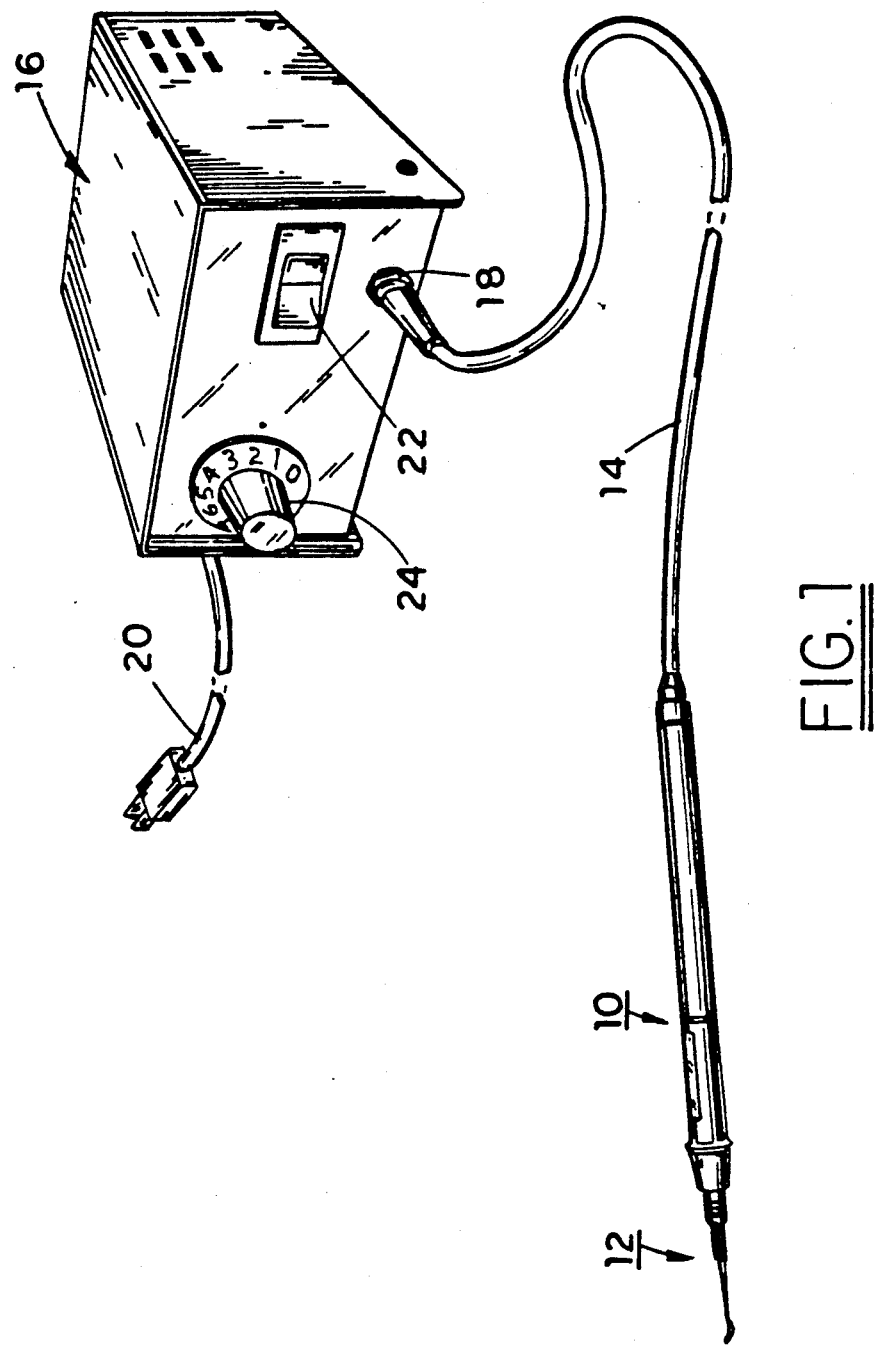
FIG. 1 illustrates an electrical temperature controlling apparatus for shaping wax tools and an attached handpiece with a wax shaping tip.

FIG. 1 is a schematic illustration of the invention in which an electrically heated handpiece 10 containing a removable wax shaping tip 12 is connected by electrical cord 14 through jack 18 to an electrical power unit 16. Power unit 16 contains an off/on switch 22 and a temperature control knob 24, and may be conveniently plugged into any suitable source of electricity through cord 20.

The power unit utilizes a transformer, potentiometer and associated solid state circuit (not shown) to provide continuous variable electric current to handpiece 10. When the handpiece is plugged into the power unit the electric current is conducted to the handpiece tip 12 via electric cord 14. As current passes through the conductive wire 42 to tip end 44 the resistance of the wire causes it to heat (see also FIG. 2).

FIG. 2 illustrates a side view of the wax shaping tool of the present invention in which handpiece 10 comprises handle section 30, a triangular cross-sectional gripping section 28 (See FIG. 4) and bezel 26 having an open cylindrical end 54 to accommodate a removable wax shaping tip 12. The opposite end 32 of the handpiece has an open end 32A to accommodate a connection for cord 14. The handpiece may be made of any suitable high temperature plastic. Suitable materials include polyester thermoplastics such as Noryl available from General Electric. Other suitable plastics include polyimides, epoxies and sulfone polymers.

In a preferred embodiment of the present invention illustrated in FIGS. 5-10, the removable shaping tip 12 of the present invention comprises a molded plug section 34 which may be of any suitable high temperature plastic such as VALOX available from General Electric or those listed above for the handpiece. The tip end portion comprises a pair of substantially parallel conductive wires 42 which end in a continuous rounded point tip of novel configuration to be described more fully herein later. The wire portion of the tip 12 may comprise any suitable conductive metal or alloy. Bare nickel-chromium wire, also referred to as Ni-chrome wire, (60% nickel, 26% chromium, 14% iron) is a preferred metal for the conductive wire portion of the removable shaping tips. The wire is preferably fine gauge such as 20, 22, 24 or 28. To enhance conductivity and provide for additional mechanical stability, wires 42 at the ends opposite the rounded tip portion 44, are encased in a larger diameter copper tube 38 which is crimped around wires 42 at 46. A partial breakaway view, FIG. 5, illustrates a suitable assembly technique in which the copper tubes 38 surround wires 42 by crimping at 46, and connect with additional conductive wires 36 by crimping at the opposite end 40. A moldable plastic plug 52 holds wires 36 in alignment. The final molded plug section is illustrated in FIGS. 6 and 7. Molded plug section 34 of the removable tip has circular grooves 34A which aid in inserting and removing the tip wires 36 into a receiving socket contained in cylindrical opening 54 of the handpiece.

The molded plug section further contains notches 48 and 50 which respectively register and mate with ridges 56 and 58, respectively, which are molded in the cylindrical opening 54 of the handpiece in a snug fit when wires 36 are inserted in electrical contacts 70, which are illustrated in FIG. 4.

FIG. 3 illustrates the positioning of the removable shaping tip 12 in opening 54 in which notches 48 and 50 are in register and held in place by ridges 56 and 58, respectively (see also FIG. 4A). Electrical connection is made between wires 36 and electrical socket 62 illustrated in FIGS. 3 and 4. The electrical circuit is completed by wire 68 which is connected to socket 62 and power unit 16 through cord 14. Bezel 26 is held in place by a press fit through collar section 66 which engages with collar section 64 of gripping section 28.

As shown in FIGS. 4A and 4, when removable tip 12 is in place in the handpiece, molded plug section 34 and the larger internal diameter of opening 54 of bezel 26 combine to form circumferentially extending air gaps 60 which provides a unique configuration for assisting in keeping the handpiece cool, such that finger gripping at section 28 is comfortable to the user. Most handpieces in the prior art become heated upon use and result in discomfort because of the high level of heat being generated to the user's hand. Furthermore, high heat generated at the tip end of wax carving tools tend to degrade components, and handpieces of this type tend to wear out in a relatively short period of time. Thus, the air gaps 60 formed by the present invention provide both user comfort and extend the life of the components of the wax shaping tool.

The wire shaping tip end of the removable shaping tips of the present invention are more clearly illustrated in FIGS. 11-16. These tips constitute a pair of substantially spaced apart parallel wires 42 spaced apart at 150, 250, 350, 450, 550 and 650, respectively, with the distance between the wires 42 being reduced towards the tip ends at 151, 251, 351, 451, 551 and 651, respectively.

As shown in FIGS. 11, 11A and 11B, a long bent tip configuration is illustrated. The tip has a double bent end section which is bent at 152 and 153, forming straight sections 154 and 155 which result in the formation of a V at bend 153. The bends 152 and 153 are at angles of about 40° and 100°, respectively to the longitudinal axis of wires 42. The space at the tip end between the substantially parallel wires 42 form a gap 156, which through capillary action or attraction, when the wire is heated, draws wax and holds it in place and provides a convenient tool for easy removable of wax, and also for adding wax to the desired model or pattern. This tip, unlike the others of the present invention, is also uniquely suited to welding two pieces of wax together. Furthermore, in a fine wire gauge, this configuration is particularly suited to glazing or smoothing the surface of wax. In use, this tip will contain wax at the complete tip end in gap 156, from bend 152 to tip end 157.

Similarly, the short bent tip of FIGS. 12, 12A and 12B is of substantially identical configuration to the tip of FIG. 11 with less overall length and is similarly bent at 252 and 253 to form straight sections 254 and 255 with a substantially identical air gap 256 which functions in a manner substantially equivalent to the long bent tip of FIG. 11, i.e., hold wax in gap 256 from bend 252 to tip end 257.

FIGS. 13, 13A and 13B illustrate a folded straight tip in which the tip is bent 180° at a curved outer end 352 and has a folded back rounded end portion 353. The gap 354 formed by the fold, through capillary action in use, can be completely filled with wax. This novel tip design holds the largest amount of wax of the tip designs of the present invention and the folded tip provides approximately four times the amount of wax as the type of tips illustrated in FIGS. 11 and 12. This tip is particularly useful in building up new areas or filling holes and making new surfaces. As in the other tips, the air gap 354 is the location where the wax is held in place by capillary action, and this tip allows the user to add and remove wax at will from a source or model.

FIGS. 14, 14A and 14B illustrate a round nose tip having an gap 452 at tip end 453 with a tip ending in a continuous curved surface 454. This tip has particular application in texturing, spuring wax patterns to sprue trees, and for building up wax. The air gap 452 formed at the end of the tip is substantially, completely filled with wax in use. The wax, as with the other tips, is drawn and held in place by capillary action when the wire is heated and the tip provides for very easy wax removable or adding wax at the discretion of the user.

FIGS. 15A, 15B and 15C illustrate an S-shaped or "squiggle" tip which is extremely convenient for building up wax, controlling wax when attaching a wax pattern to a sprue, making ring shanks out of the wax, and texturing and sculpturing wax models. The double air gap 552 formed by the S configuration is completely filled with wax by capillary action in use and allows the user to add and remove wax at will. The tip end surfaces 553 have the curvature essentially that of a circle. This S-shaped tip functions similarly to the folded straight tip of FIG. 13, and holds almost as much wax and provides for good wax control.

FIGS. 16, 16A and 16B illustrate a rolled flat spatula tip. This tip may conveniently be used for building wax up and removing wax, filling holes and gaps, making new surfaces, texturing, scooping, molding and cutting wax. The tip comprises two substantially rolled flat sections 652 ending in a rounded point 653 and containing a fine internal V groove 654 which draws and holds wax through capillary action. Optionally, the tip may contain longitudinal grooves in the flat surfaces 652 on both sides, which allow the tip to hold additional wax. This grooved feature is not shown by the drawings.

A substantially uniform gap width between the wires 42 for gaps 156, 256, 354, 452 and 552 for tip ends of FIGS. 11-15, respectively, ranges from about 0.015 to 0.040 inches. A preferred width of about 0.020 to 0.030 inches insures good capillary action in use.

The length of the wire portion of the tips of the present invention is from about 1.5 to 3.50 inches. The distance between wires 42 at their spaced apart parallel locations 150, 250, 350, 450, 550 and 650, respectively ranges from about 0.075 to 0.20 inches. A distance of about 0.10 has been found satisfactory for most wire gauges.

In general, the temperature of the tips in use are controlled from between about 150° to 1000° F., depending upon the function being performed.

For example, when softening or melting wax, a temperature at the lower end of the range is usually used, while for cutting or glazing wax, a temperature at the higher end of the range is used. For most other uses temperatures in the middle of the range can be used.

Although particular embodiments of the present invention have been disclosed herein for purposes of explanation, further modifications or variations thereof will be apparent to those skilled in the art to which this invention pertains.

What is claimed is:

1. A tool suitable for shaping wax substances comprising:
    a) an elongated handpiece for supporting an electrically conductive tool tip having a forward end and a rear end;
    b) means in said handpiece for electrical connection to a source of electrical power;
    c) the portion of said handpiece adjacent said front end having a triangular transverse cross-section for defining a gripping section;
    d) said handpiece having a front end section forward of said gripping section which has an opening and means within said opening for receiving and supporting a removable a wax shaping tip in a fixed predetermined position extending forwardly from the front end of said handpiece;
    e) said tip including a mounting plug section insertable into the front opening of the handpiece, and supported by said receiving and supporting means of said handpiece with said mounting plug section of the tip and the receiving and supporting means of the handpiece having interlocking means for securing the tip in a predetermined position in the handpiece; with said interlocking means further defining cooling air gaps between the outer surface of the mounting plug section and the surfaces of the receiving and supporting means; and
    f) said tip comprising two spaced apart conductive wires carried by the mounting plug and having a rear end connected to said connection means in said handpiece when the mounting plug is mounted in the receiving and supporting means; with the front ends of the wires being joined and shaped to form a continuous tip end portion which defined configuration is capable of holding and shaping wax.

2. The tool of claim 1 in which the tip end portion comprises two consecutive bent sections, both bends being at an angle from the longitudinal axis of the body section of said tip wires defining a gap in the form of a V.

3. The tool of claim 1 in which the tip configuration comprises a folded tip end portion at an angle of about 180° from the longitudinal axis of the body section of said tip wires, said folded portion forming an elongated gap which is defined by four wire sections.

4. The tool of claim 1 in which the tip end portion comprises a rounded nose portion having a curvature in the form of a partially completed circle which forms an internal gap.

5. The tool of claim 1 in which the tip end portion comprises a double rounded nose section in the form of an S which defines an internal gap.

6. The tool of claim 1 in which the tip end portion comprises two flattened spatula end sections having a rounded end point and a reduced internal gap in the form of a fine V.

* * * * *